United States Patent [19]

Collins et al.

[11] Patent Number: 4,531,411
[45] Date of Patent: Jul. 30, 1985

[54] ACOUSTIC EMISSION LINEAR PULSE HOLOGRAPHY

[75] Inventors: H. Dale Collins; Lawrence J. Busse, both of Richland; Douglas K. Lemon, West Richland, all of Wash.

[73] Assignee: The United States of America as represented by the United States Department of Energy, Washington, D.C.

[21] Appl. No.: 545,426

[22] Filed: Oct. 25, 1983

[51] Int. Cl.³ .......................................... G01N 29/04
[52] U.S. Cl. .................................... 73/603; 73/587
[58] Field of Search .................... 73/603, 587, 799

[56] References Cited

U.S. PATENT DOCUMENTS 4,170,142 10/1979 Posakony et al. .................... 73/603
4,353,255 10/1982 Fukuda et al. ........................ 73/587
4,459,851 7/1984 Crostack ............................... 73/587

Primary Examiner—Anthony V. Ciarlante
Attorney, Agent, or Firm—Edward W. Nypaver; Robert Southworth, III; Judson R. Hightower

[57] ABSTRACT

Defects in a structure are imaged as they propagate, using their emitted acoustic energy as a monitored source. Short bursts of acoustic energy propagate through the structure to a discrete element receiver array. A reference timing transducer located between the array and the inspection zone initiates a series of time-of-flight measurements. A resulting series of time-of-flight measurements are then treated as aperture data and are transferred to a computer for reconstruction of a synthetic linear holographic image. The images can be displayed and stored as a record of defect growth.

5 Claims, 24 Drawing Figures

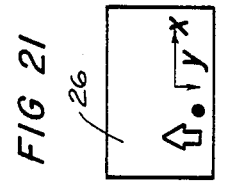
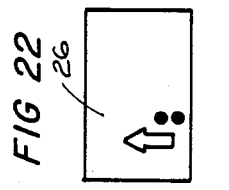
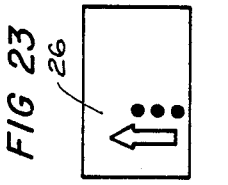
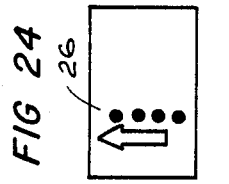
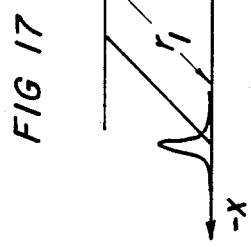
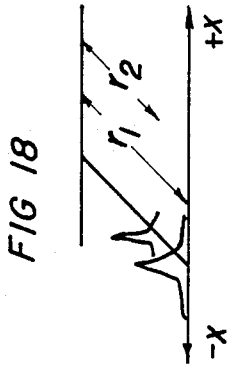
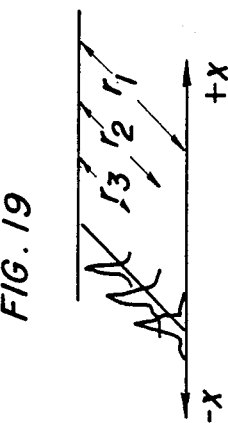
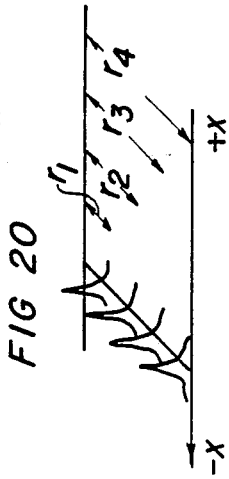
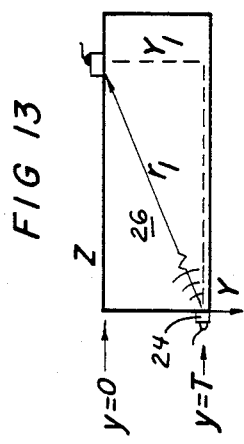
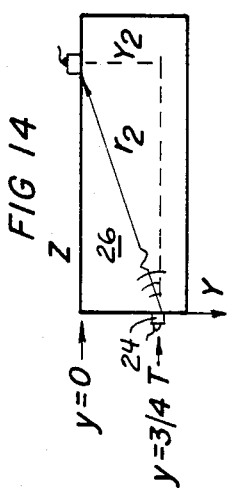
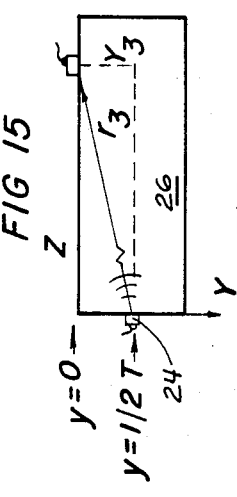
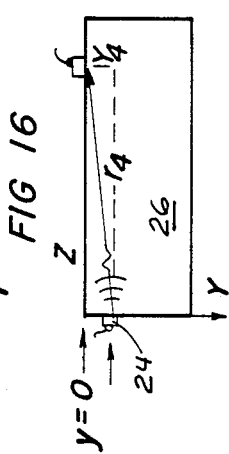

ACOUSTIC EMISSION LINEAR PULSE HOLOGRAPHY

The United States Government has rights in this invention pursuant to Contract No. AT (45-1)-1830 between the U.S. Department of Energy and Battelle Memorial Institute.

BACKGROUND OF THE INVENTION

This relates to the concept of and means for performing Acoustic Emission Linear Pulse Holography, which combines the advantages of linear holographic imaging and acoustic emission testing into a single non-destructive inspection system. This unique system produces a chronological, linear holographic image of a flaw by utilizing the acoustic energy emitted during crack growth.

Conventional linear holographic imaging uses an ultrasonic transducer to transmit energy into the volume being imaged. When the crack or defect reflects that energy, the crack acts as a new source of acoustic waves. To formulate an image of that source, a receiving transducer is scanned over the volume of interest. The phase of the received signals is then measured at successive points on the scan. The phase information can be reconstructed to formulate an image of the defect.

Conventional acoustic emission testing methods utilize the energy given off by a crack as it grows in a monitoring system to detect and locate it. This is done by measuring the time of arrival of an elastic wave at a group of sensors (usually 2 to 4) and then computing the crack location by using triangulation or other computational techniques. Typically the location accuracy is no better than one wall thickness. No direct measure of crack size can be obtained by such systems.

The innovation disclosed in this disclosure is the concept of utilizing the crack-generated acoustic emission energy to generate a chronological series of images of a growing crack by applying linear, pulse holographic processing to the acoustic emission data. The process is implemented by placing on a structure an array of piezoelectric sensors (typically 16 or 32 of them) near the defect location. A reference sensor is placed between the defect and the array.

The short bursts of acoustic emission generated by stress, etc, propagate through the medium to the discrete-element receiver array. The reference timing sensor that is positioned between the array and the inspection zone initiates time-of-flight measurements to each sensor in the array. The acoustic wave signals are sampled at each position across the array and time-of-flight data are measured at each position. The aperture data (i.e., series of measurements) are then transferred to a computer for reconstruction of a timed series of linear holographic images. Computer reconstruction of the images can be accomplished using a one dimensional FFT algorithm. Images can be displayed on the computer terminal graphics console. All image data can be stored on digital tape cartridges to allow generation of a chronological history of crack growth with respect to the material depth, etc.

The general concept of using short ultrasonic pulses to generate synthetic frequency holograms was first presented with respect to underground mining applications and later applied to imaging of underground pipes. However, in these conventional techniques a pulse of ultrasound energy is transmitted into the medium being inspected and then the time until the arrival of the returned echo is measured. Acoustic emission Linear Pulse Holography differs from conventional linear pulse holography in that the acoustic energy emitted by the defect itself is used to generate the time-of-flight information to a receiving array of sensors.

Conventional acoustic emission monitoring performs source location by measuring the time of arrival of an acoustic emission wavefront at 2 to 4 sensors. The time information is used indirectly to estimate the location of the source. This method only locates the general area from which the sound wave originated. It does not give image-type information about the shape and growth of the actual crack front. Hence, acoustic emission Linear Pulse Holography differs from conventional acoustic emission monitoring in that (1) linear pulse holographic techniques are used to locate the source, rather than for time triangulation computations, and (2) acoustic emission Linear Pulse Holography has sufficient resolution to continuously image the changing shape of a crack front or defect boundary.

SUMMARY OF THE INVENTION

The aspects or features of acoustic emission Linear Pulse Holography that we consider to be novel or useful advances over prior technology are:
1. The use of the crack-generated acoustic energy as the source for generating a computer reconstructed image of the source point.
2. Application of linear pulse holography techniques to acoustic emission data obtained by an image array of sensors to formulate an image and time history of entire crack front.

Acoustic Emission Linear Pulse Holography combines the advantages of holography and acoustic emission systems into a single process. Acoustic emission monitoring has the advantage of being a passive, continuous process; the drawback is the difficulty in making quantitative interpretations of the data. Conventional holographic imaging provides accurate information about flaw size, but such imaging is only done periodically; mechanical scanners must be mounted on the structure and operated by remote control. By imaging with acoustic emission holography, one can accurately image a dynamic (i.e., growing) flaw and also have the benefit of doing so continuously and remotely.

Therefore the advantages of acoustic emission Linear Pulse Holography are:

Continuous Monitoring: The image of a flaw is continuously updated as it grows. Hence, operating personnel are continually aware of the status of a flaw in a critical structure. This enhances safety and reliability.

Simplicity: The system has no moving parts and hence conventional scanners are not needed. Other acoustic emission monitoring systems on the structure may be used, in part, in the acoustic emission Holography System. These simplifying features reduce the cost of implementation, use and maintenance.

This new technique would be most advantageously applied in situations where continuous monitoring of a defect is desirable, but is impractical to do with manual or mechanical techniques. For example, suppose a flaw were to be found in a nuclear reactor pipe, pressure vessel, or nozzle, but were small enough that immediate repair was not required. Use of the present technique would allow the growth of the flaw to be monitored continuously during subsequent operational periods.

Conventional ultrasonic imaging can not be accomplished during operation. Conventional acoustic emission monitoring can not produce quantitative information about crack size and growth rate.

Similarly, the present acoustic emission holography technique could be used to monitor remote but critical locations in aircraft, ships or submarines. The technique could also continuously monitor crack grown in offshore drilling platforms, where manual inspection by divers is expensive, hazardous, and necessarily periodic. A continuous monitoring and imaging system could provide valuable information about growth of a critical crack that would otherwise be unavailable. In each case, having continuously updated information may allow one to avert a structural failure that might otherwise occur.

Additional objects, advantages and novel features of the invention will be set forth in part in the description which follows, and in part will become apparent to those skilled in the art on examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention as embodied and broadly described herein, the apparatus of this invention may comprise a method for monitoring and imaging growing defects in a structure including the steps of mounting discrete sensors about the structure for detecting acoustic waves as an output pulse at each sensor, the step of determining the relative phase of the output pulse of each sensor at a selected time as a function of its transmission time from the defect to the sensor, subsequent combining of the resultant accumulative phase information into a synthetic hologram, and reconstruction of the hologram into an image of the defect.

The apparatus described herein comprises a plurality of discrete sensors arranged in a preselected geometric array on the surface of the structure being tested, each sensor having the capability of detecting acoustic waves emitted from the defect as an output pulse, means for determining the relative phase of the output pulse of each sensor at a selected time as a function of its time-of-flight, an information processor for combining the accumulative phase information into a synthetic hologram of the defect and equipment for reconstructing the hologram into an image of the defect.

BRIEF DESCRITION OF THE DRAWINGS

The accompanying drawings, which are incorporated into and form a part of the specification, illustrate an embodiment of the present invention plus available test data and, together with the description, serve to explain the principles of the invention. In the drawings:

FIGS. 13 through 16 are a sequence of side views corresponding to growth of a defect;

FIGS. 17 through 20 are a series of Acoustic Energy Linear Holographic amplitude reconstructions corresponding respectively to FIGS. 13 through 16; and FIGS. 21 through 24 are a series of simulated end view images illustrating defect propagation and corresponding respectively to FIGS. 13 through 16.

DETAILED DESCRIPTION OF THE INVENTION

This disclosure relates to a unique technique for imaging defects due to fatigue, cracks, etc. as they propagate with time. It uses their emitted acoustic energy (i.e., acoustic emission) as the source. The short bursts of acoustic energy generated by stress, etc. propagate through the medium to a discrete element receiver array. A reference timing transducer positioned between the array and the inspection zone initiates time-of-flight measurements to the individual sensors. The received signals are sampled at different positions across the array and time-of-flight data measurements are measured at each position. The aperture data (i.e. series of time-of-flight measurements) are then transferred to a computer for reconstruction of a linear holographic image. Computer reconstruction of the images can be accomplished using a one-dimensional algoithm. Image data can be displayed on the computer terminal graphic console. All image data can be stored on digital tape cartridges to allow generation of a chronologocial history of crack growth with respect to the material depth, etc.

Figure 1:
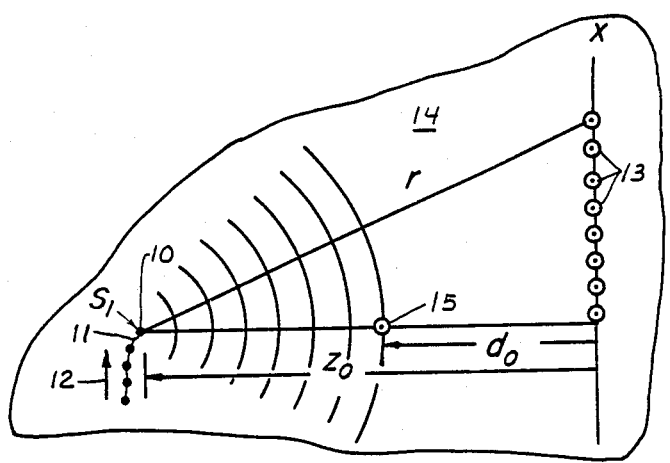
FIG. 1 is a schematic illustration of crack growth, simulated by a series of point source emissions.

The concept behind acoustic emission Linear Pulse Holography is illustrated in FIG. 1. As a crack grows, each small segment of the crack front emits acoustic waves. FIG. 1 schematically illustrates emissions in the form of bursts coming from the crack 11 in a wall segment 14; hence, one can consider the crack front to be a group of sources 10. The direction of crack propagation is shown by arrow 12. When, for example, the source segment $S_1$ emits, the resulting acoustic wave is detected at each sensor 13 in the array. The relative phase of the pulse at each sensor 13 can then be determined in relation to a reference sensor 15. As each source 10 emits, the cumulative phase information can be combined into a phase image or hologram of the sources 10. The hologram can then be reconstructed into an image where each source segment has a counterpart in the total reconstructed image.

As the crack 11 grows over a period of time, an image can be constructed of it. This provides information on the length of the crack and its growth rate.

Figure 5:
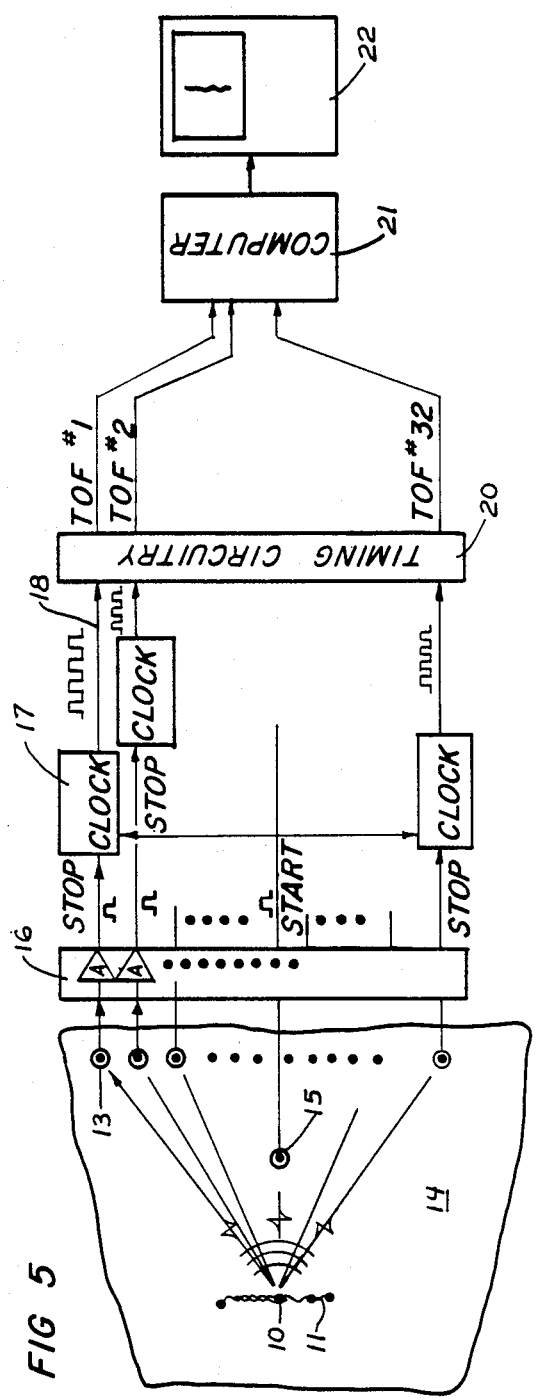
FIG. 5 is a block diagram of a data acquisition and display system for implementing the present system of acoustic emission Linear Holography.

A block diagram of a data acquisition system to implement this concept is shown in FIG. 5. The acoustic emission burst from the crack 11 propagates and is detected by the array of transducers 13. Each transducer 13 has a separate processing channel consisting of a receiver 16, clock 17, etc. The channel outputs 18 are converted into time-of-flight data by timing circuitry 20 and transferred to a computer 21 for reconstruction by a linear image display 22.

The data are defined by Equation (1) which relates the time-of-flight in terms of the propagation velocity ($v_p$) and the crack emission position to array element distance ($r_i$):

$$TOF = 1/v_p [r_i - (Z_o - d_o)] \tag{1}$$

where $r_i = [Z_o^2 + X_i^2]^{\frac{1}{2}}$ and $v_p$ = propagation velocity.

Figure 2:
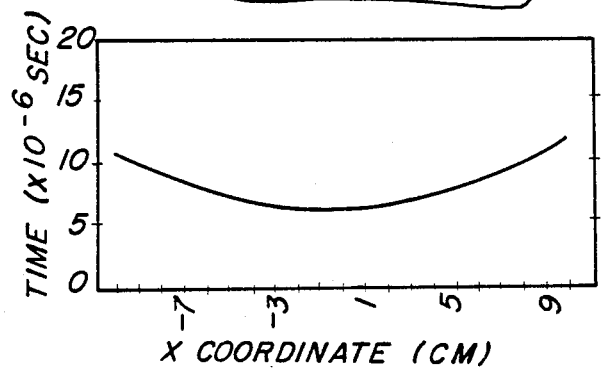
FIG. 2 is a plot of a typical time-of-flight profile across a linear apeture.

FIG. 2 is a typical time-of-flight profile. Holography is based upon the measurement of phase rather than pulse transit time. Therefore, the time-of-flight information can be synthetically converted into phase data by the following relationship:

$$\phi = \omega t \tag{2}$$

where $\omega$ = radian frequency. The phase components, as required for digital reconstruction, with their selected synthetic frequency are defined by the two simple equations:

$$f_r(x) = K\cos\omega \left\{ \frac{1}{v_p} [(X_i^2 + Z_o^2)^{\frac{1}{2}} - (Z_o - d_o)] \right\} \tag{3}$$

$$f_i(s) = K\sin\omega \left\{ \frac{1}{v_p} [(X_i^2 + Z_o^2)^{\frac{1}{2}} - (Z_o - d_o)] \right\} \tag{4}$$

Figure 3:
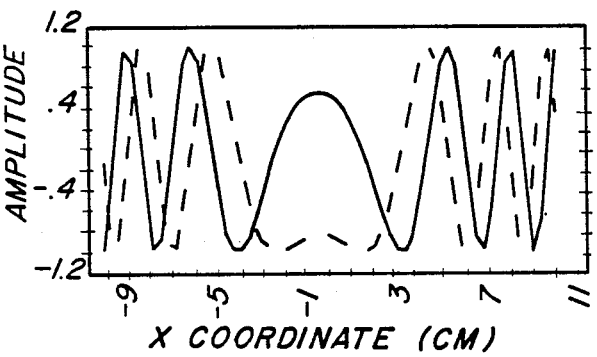
FIG. 3 is a plot of the fresnel zone phase pattern corresponding to the time data in FIG. 2.
Figure 4:
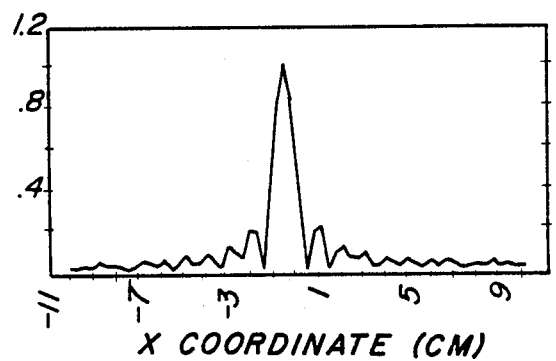
FIG. 4 is a linear, holographic reconstruction of the image based on the fresnel zone phase patterns shown in FIG. 3.

A plot of Equations (3) and (4), shown in FIG. 3, yields curves equivalent to a fresnel zone pattern or point object hologram. Thus, by proper signal processing of the acoustic emission time-of-flight data, it can be converted to holographic format and the linear image can be reconstructed as shown in FIG. 4.

The choice or selection of the maximum synthetic frequency and array element spacing is not completely arbitrary, but depends on three important parameters: pulse bandwidth, propagation velocity, and source-to-hologram distance.

With pulse systems, the pulse bandwidth (B) or rise time $\tau$ is a function of the timing accuracy (i.e., detection jitter). Typically, the resultant time jitter in acoustic emission pulse detection systems, is usually about one-hundredth of the rise time (i.e., $0.01\tau$). While sophisticated correlation techniques can reduce this error, this value will be assumed to be adequate in the following array element spacing analysis. The propagation velocity multiplied by the detection jitter is the associated position error in the time-of-flight measurements. Thus, these two parameters will be involved in the expression for the minimum selectable element spacing. The remaining parameter, source-to-hologram distance, determines the time delay or phase between array elements. The greater the distance, the less time delay between elements. If the point source is at infinity, a plane wave exists across the array (i.e., no time variation). So it would be expected that this parameter would be in the final expression of array element spacing and frequency selection.

Figure 6:
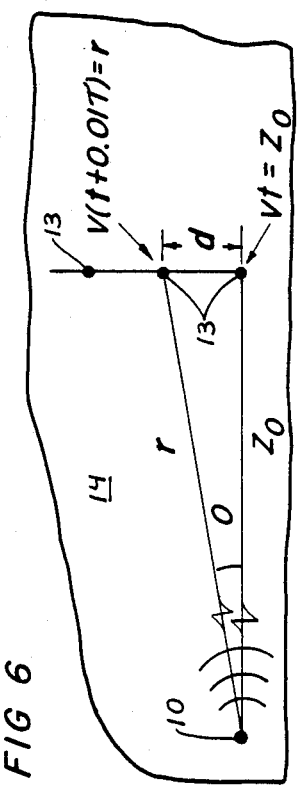
FIG. 6 is a schematic diagram of the pulse-receiving array geometry used to determine the maximum synthetic frequency.

FIG. 6 shows the pulse receiving array geometry used in the analysis where the source-to-array distance, assuming paraxial approximation is:

$$r \simeq Z_o + \frac{1}{2} \frac{d^2}{Z_o} \tag{5}$$

and d = array element spacing.

The minimum detectable time difference between elements is assumed to be $0.01\tau$, and the following equation defines the relationship mathematically:

$$v_p(.01\tau) \simeq \frac{1}{2} \frac{d^2}{Z_o} \tag{6}$$

where $\tau$ is the pulse rise time (=0.35/B) and B is the pulse bandwidth.

The array spacing d is easily determined by equation (6)

$$d \gtrsim 0.08 \left( \frac{Z_o v_p}{B} \right)^{\frac{1}{2}}. \tag{7}$$

The relationship between the array receiver spacing and f can be derived by the sampling theory, where the highest spatial frequency must be sampled at least two times per cycle. This can be expressed by the following equation:

$$d \leq \lambda/2 \tag{8}$$

and the selectable frequencies $$f \leq 6.25 \left( \frac{v_p B}{Z_o} \right)^{\frac{1}{2}} \tag{9}$$

A typical example using acoustic emission data from a 10 cm thick steel plate would yield:

$Z_o$ = 30.48 cm
$v_p$ = 3.17 mm/$\mu$sec, and
B = 0.8 MHz

Using equation (7) and (8), the calculated array spacing (d) is 2.7 mm, and the maximum selectable frequency (f) is 570 kHz.

Thus, a system timing jitter of $0.01\tau$ and the two parameters ($v_p, Z_o$) uniquely define the receiver spacing and the maximum equivalent holographic continuous wave frequency.

Figure 7:
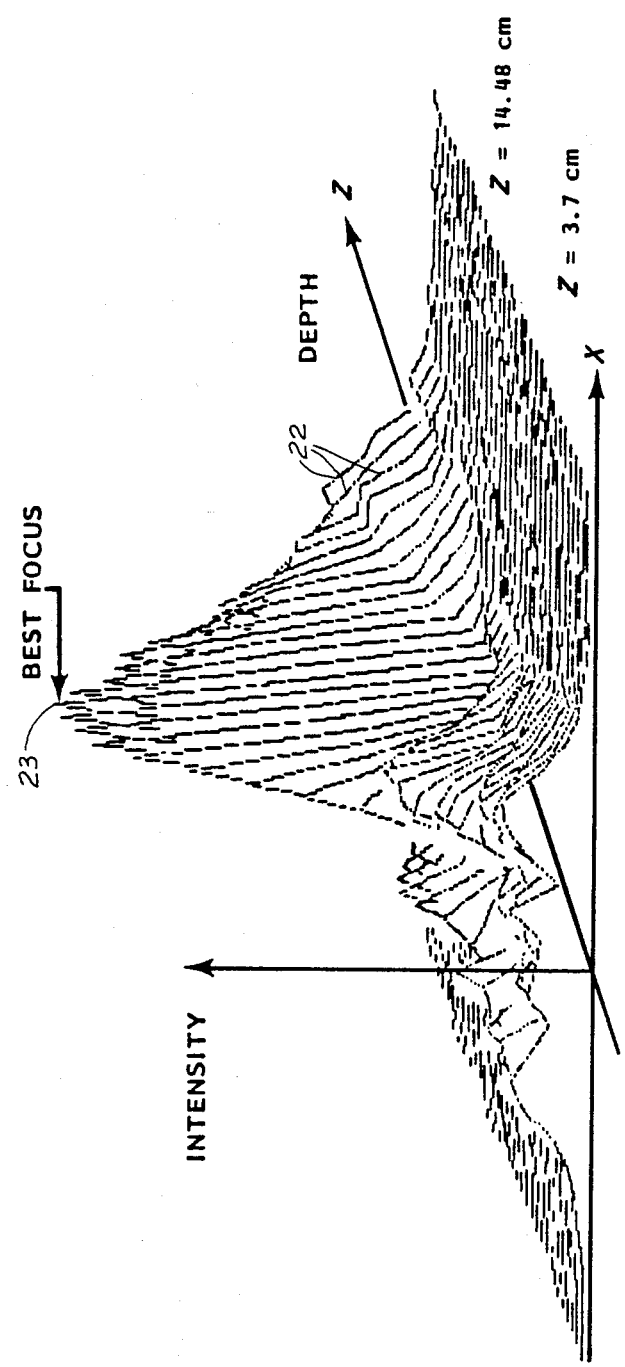
FIG. 7 is a plot of sequential isometric images of point source data, showing the concept of optimum focusing.

The acoustic emission source location algorithm predicts the position of the emission source within the medium by sequential image reconstruction at preselectable depth intervals. The predicted depth or range is then determined by where the optimum focus occurs. FIG. 7 illustrates this concept of optimum or best focus using an isometric display of the reconstructed source amplitude or intensity function.

The data displayed in FIG. 7 is based on calculations involving one measurement taken at each of 32 points in a receiver array. The synthetic frequency chosen was 0.75 MHz. The sampling interval was 0.635 cm. The reconstruction distance was 14.48 cm and the velocity of sound propagation in the specimen was taken to be 0.610 cm/μsec.

Each line 22 in FIG. 7 represents a discrete depth increment of 0.635 cm starting at 3.7 cm from the array. The distribution peaks at 23, where best focus occurs as shown. The predicted depth is at 14.5 cm or at about the middle of the distribution.

The isometric focus/depth graphic display program can be used effectively in determining the acoustic emission source position within the test medium.

In order to verify the concept of acoustic emission Linear Pulse Holography, some means of making time-of-flight measurements was needed. Since the equipment to make multiple simultaneous time-of-flight measurements was not readily available, we modified existing equipment to make a single time measurement between a reference sensor and one array sensor. The array sensor was initially placed at one end of the linear aperture and a measurement made. Then the sensor was moved to the next position and another measurement made. In this way, we gradually accumulated the needed time-of-flight information. The system shown in FIG. 5 would acquire simultaneous measurements from all sensors from a single acoustic emission event.

The acoustic source in our first experiments was a piezoelectric transducer 24 (FIGS. 12-16) driven by a voltage pulse. This ensured that the same source waveform was emitted through specimen 26 for each measurement at the array locations simulated by a movable sensor 25. With simultaneous, multi-channel recording, one image point is obtained for each acoustic emission event. Since we had to build up data one location at a time, a reproducible source function ensured that this temporary technique was representative of the ultimate hardware system performance.

The first experiments consisted of verifying the various basic linear image parameters using a simulated acoustic emission source positioned on a flat aluminum plate 30 to 60 cm from the array.

Figure 8:
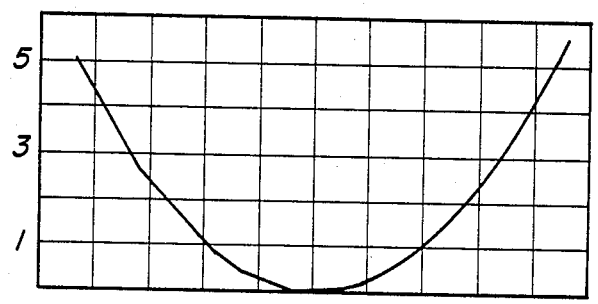
FIG. 8 is a plot of an experimental time-of-flight profile.
Figure 9:
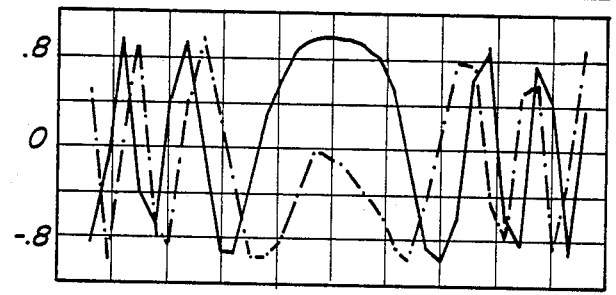
FIG. 9 is a plot of the fresnel zone phase patterns corresponding to FIG. 8.
Figure 10:
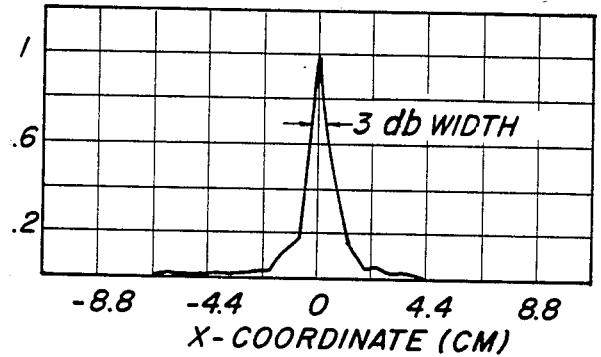
FIG. 10 is a plot of the reconstructed image resulting from the fresnel zone phase patterns shown in FIG. 9.
Figure 12:
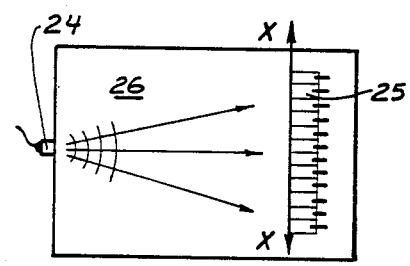
FIG. 12 is a schematic top view of a simulated test apparatus to illustrate chronological image sequencing of a defect.

FIGS. 8, 9 and 10 illustrate the digital image reconstruction sequence of the acoustic emission source positioned on the plate surface 30 cm from a 32 point array. The minimum array element spacing was 0.27 cm using the given image parameters: $v_p = 0.317$ cm/μsec, $Z_o = 30$ cm, $B = 0.8$ MHz. The actual sampling (0.635 cm) for this experiment was determined by the dimensions of the acoustic emission elements. The selected synthetic reconstruction frequency using one wavelength sampling between elements was approximately 0.5 MHz. The actual sampling interval was 0.635 cm. The reconstruction distance was 30.48 cm and the velocity of sound was taken as 0.317 cm/sec. FIGS. 9 and 10 are the quadrature components and the reconstructed image respectively.

The 3 dB amplitude width (FIG. 10) which defines the source holographic lateral image resolution is 6 mm. The theoretical predicted resolution using equation (10) is approximately 8 mm, which compares very nicely with the experimental results.

FIGS. 13–24 illustrate graphically the chronological image sequence of a simulated crack growing from the bottom to the upper surface in a test block 26. The time series of isometric amplitude plots and their corresponding point images were integrated into a single composite crack image defining the physical length in terms of its acoustic energy emissions.

The sequence started with the acoustic emission source 24 positioned at the bottom face (y=T) of a 10 cm thick aluminum block 26 simulating the crack initiation point. The corresponding linear image is a single point (see FIG. 21). As the crack propagates acoustic energy upward, the acoustic energy emissions occur at different positions, ($\frac{3}{4}T$, $\frac{1}{2}T$, etc.), until they stop at $\frac{1}{4}T$ (See FIGS. 22–24). The integrated sequential image which results uniquely defines the dynamic crack growth length.

Figure 11:
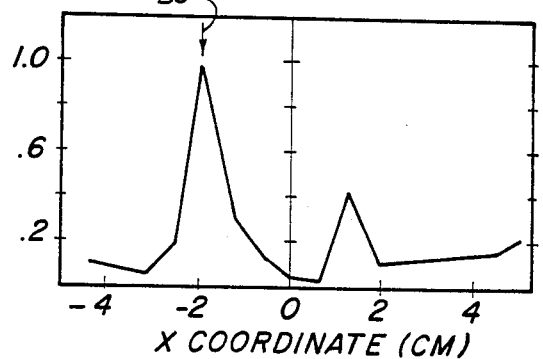
FIG. 11 is a linear reconstruction image of data taken on a test specimen.

In a separate test, a small fatigue crack was visible in an aluminum test specimen (not shown) after stress cycling. This crack was imaged as it grew and propagated horizontally toward the plate edge. FIG. 11 illustrates an image of this crack tip when the crack length was 2 cm. The position of the tip is indicated by arrow 30. This type of image allows for precise location of the "active" portion of a growing crack at any instant in time. Integration of many such images during the course of stress cycling would provide a record of total crack growth. Hence, the concept has been tested and shown to be feasible when applied to acutal crack acoustic emissions.

The foregoing description of the preferred embodiments of the invention has been presented for purposes of illustration and description. It is not intended to be exhaustive or to limit the invention to the precise form disclosed, and obviously many modifications and variations are possible in light of the above teaching. The embodiments discussed in detail were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A method for monitoring growing defects in an inspection zone within a structure, comprising the following steps:

mounting a plurality of discrete sensors, including a reference sensor, at fixed locations in a preselected array along a surface of the structure adjacent to the inspection zone;

detecting the acoustic waves emitted from a growing defect in the inspection zone as output pulses generated at each sensor;

determining the phase components of the output pulse generated at each sensor at a selected time as a function of the pulse transmission time between the sensor and the reference sensor and as a function of a synthetic frequency selected from the pulse bandwidth; and combining the resulting cumulative phase information into a synthetic hologram of the defect.

2. The method of claim 1, wherein the step of determining the phase components of the output pulse is repeated at selected intervals over a period of time.

3. The method of claim 1, further comprising the following step:

reconstructing the synthetic hologram into an image of the defect.

4. The method of claim 1, further comprising the following step:

reconstructing the hologram into sequential images of the defect at preselected depth intervals within the structure; and determining the depth of the defect relative to the surface of the structure on which the sensors are mounted by identifying the depth at which the sequential image reconstruction achieves optimum focus.

5. An apparatus for monitoring growing defects in an inspection zone within a structure, comprising:

a plurality of discrete sensors, including a reference sensor, mounted at fixed locations in a preselected array along a surface of the structure adjacent to the inspection zone, each sensor having the capability of detecting acoustic waves emitted from a growing defect within the structure as an output pulse;

means for determining the phase components of the output pulses generated at each sensor at a selected time as a function of the pulse transmission time between the sensor and the reference sensor and as a function of a synthetic frequency selected from the pulse bandwidth;

and means for combining the resulting cumulative phase information into a synthetic hologram of the defect.

* * * * *